United States Patent
Krantz et al.

Patent Number: 5,527,324
Date of Patent: Jun. 18, 1996

[54] SURGICAL STENT

[76] Inventors: Kermit E. Krantz, 6711 Overhill Rd., Mission Hills, Kans. 66208; Joe D. Dennis, 6600 W. 95th St., Overland Park, Kans. 66212

[21] Appl. No.: 301,659

[22] Filed: Sep. 7, 1994

[51] Int. Cl.⁶ ................................................. A61B 17/00
[52] U.S. Cl. ........................ 606/155; 606/151; 606/153; 606/154; 623/12
[58] Field of Search ........................ 606/151, 153–156; 623/1, 12

[56] References Cited

U.S. PATENT DOCUMENTS

| | | |
|---|---|---|
| 1,470,707 | 10/1923 | Bates . |
| 2,428,918 | 10/1947 | Miller . |
| 3,620,218 | 11/1971 | Schmitt et al. . |
| 3,683,926 | 8/1972 | Suzuki . |
| 4,630,608 | 12/1986 | Arroyo ................................. 606/155 |
| 4,929,240 | 5/1990 | Kirsch et al. ........................ 606/155 |
| 5,064,057 | 11/1991 | Iwatsuki et al. . |
| 5,139,505 | 8/1992 | Palmieri ............................... 606/154 |
| 5,383,927 | 1/1995 | De Goicoechea et al. .......... 623/12 |

FOREIGN PATENT DOCUMENTS

| | | | |
|---|---|---|---|
| 2034413 | 1/1972 | Germany ............................. 606/154 |
| 2547265 | 4/1977 | Germany ............................. 623/12 |
| 1008193 | 10/1965 | United Kingdom ................. 606/151 |
| W092/09311 | 6/1992 | WIPO .................................. 623/12 |

*Primary Examiner*—Gary Jackson
*Assistant Examiner*—Jeffrey A. Schmidt
*Attorney, Agent, or Firm*—Hovey, Williams, Timmons & Collins

[57] ABSTRACT

A surgical stent is provided for use in supporting the walls of a tubular organ during anastomosis. The stent includes a tubular body having a diameter adapted to be about equal to the diameter of the organ and having opposed axial ends a circumferential ridge intermediate the ends. The ridge has a diameter adapted to be greater than the diameter of the tubular organ so that when the tubular organ is supported on the body, the ends of the tubular organ may be joined together along the ridge, and are everted to facilitate suturing.

6 Claims, 1 Drawing Sheet

SURGICAL STENT

BACKGROUND OF THE INVENTION

1. Field of the Invention

The present invention relates generally to prosthetic devices, and more particularly to a surgical stent for use in supporting the walls of a tubular organ during anastomosis.

2. Discussion of the Prior Art

It is conventional to provide a simple tube or ring for use during anastomosis to position two ends of a tubular organ together during suturing. Various shapes and materials are employed in conventional devices with the goal of providing support to the organ ends during anastomosis. In addition, certain conventional constructions also seek to provide a coupling for holding the ends of the organ together so that suturing is not necessary.

Several problems are presented by the available prosthetic devices. For example, although such conventional devices support the organ wall at the ends being joined, they do not positively position the intimae of the organ ends against one another. As a result, sutures must be used to accomplish this joining of the intimae.

Further, conventional devices fail to provide any means for insuring that a suture will be passed completely through the intimae of the ends of the organ without penetrating the opposite wall of the organ. Thus, when such devices are used in very small diameter organs, such as small blood vessels and the like, there is a possibility that the vessel will be stitched shut during suturing.

OBJECTS AND SUMMARY OF THE INVENTION

It is an object of the present invention to provide a surgical stent for use in supporting the walls of a tubular organ during anastomosis, wherein the stent is easy to use, and presents the ends of the organ in such a way as to reduce the risk that a suture will pass completely through opposing walls of the organ.

It is another object of the present invention to provide a stent that positively positions the intimae of the ends of the organ against one another at the time of suturing, and causes the intimae at the ends of the organ to move toward and against one another as the stent dissolves. In this manner, reproduction of the intima cells and healing of the joint is facilitated.

In accordance with these and other objects evident from the following description of a preferred embodiment of the invention, a surgical stent is provided for use in supporting the walls of a tubular organ during anastomosis. The stent includes a tubular body having a fixed, predetermined diameter adapted to be about equal to the diameter of the organ to be supported, the body having opposed axial ends and a circumferential ridge intermediate the ends. The ridge of the body is of a diameter adapted to be greater than the diameter of the tubular organ so that when the tubular organ is supported on the body, the ends of the tubular organ may be joined together along the ridge, and are everted to facilitate suturing.

By providing a construction in accordance with the present invention, numerous advantages are obtained. For example, by providing a stent having a tubular body of a fixed, predetermined diameter, a relatively rigid brace is defined on which the walls of the tubular organ are supported during anastomosis.

Further, by providing a stent with a tubular body having a circumferential ridge intermediate the ends, a construction results which everts the ends of a tubular organ when the ends of the organ are positioned on the stent for suturing. In this manner, the suturing process is facilitated and each suture is easily passed completely through the intima of each end of the organ without also penetrating the opposite wall of the organ.

In accordance with another aspect of the invention, a method of joining two ends of a tubular organ together comprises the steps of placing the ends of the organ over the opposed ends of a tubular body having a fixed, predetermined diameter, and including a circumferential ridge intermediate the ends, pushing the ends of the organ into contact with one another atop the ridge of the tubular body so that the ends of the organ are everted, and suturing the ends of the organ together through the ridge of the tubular body. Thus, the tubular body supports the organ during suturing, again providing the advantages discussed above with reference to the inventive stent.

BRIEF DESCRIPTION OF THE DRAWING FIGURES

A preferred embodiment of the present invention is described in detail below with reference to the attached drawing figures, wherein.

DETAILED DESCRIPTION OF THE PREFERRED EMBODIMENT.

Figure 1:
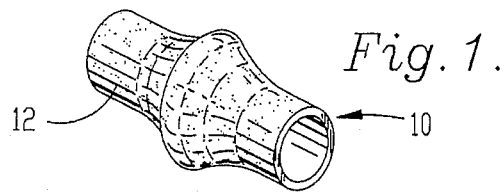
FIG. 1 is a perspective view of a stent constructed in accordance with the preferred embodiment.

A surgical stent 10 constructed in accordance with the preferred embodiment is illustrated in FIG. 1, and is designed for use in supporting the walls of a tubular organ during anastomosis. The stent is described with reference to the anastomosis of blood vessels, but it is understood that the invention also has utility in any other application involving the joining of tubular organs.

The stent 10 includes a tubular body having a fixed, predetermined diameter adapted to be about equal to the diameter of the organ to be joined. Thus, in order to provide a stent for use in an organ of a particular diameter, it is necessary to manufacture the stent of a corresponding size. Adjustment of the diameter of the stent, once manufactured, is not desired as this would reduce the level of support provided by the stent to the walls of the organ during anastomosis.

For any given size of organ, the stent is constructed of a particular diameter, length and thickness. The preferred diameter of the stent is about equal to the diameter of the organ. By providing the stent with an outer diameter substantially equal to or slightly less than the inner diameter of the tubular organ, placement of the stent within the ends of the organ is facilitated.

The length of the stent is chosen to present a central, circumferential ridge 12 intermediate the ends thereof, and a pair of tubular end sections 14 which support the tubular organ as the stent is pushed into the ends of the organ and sutured. If the stent is too short, the walls of the organ will not be sufficiently supported during suturing, and the intimae of the ends of the organ may pull apart from one another. If the stent is too long, excess stent material is placed within the organ than is necessary.

Figure 2:
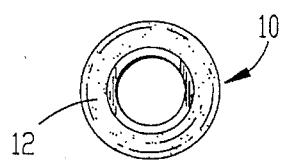
FIG. 2 is an end elevational view of the stent.

The circumferential ridge 12 is illustrated in FIG. 2, and is formed of a diameter adapted to be greater than the diameter of the tubular organ so that when the tubular organ is supported on the body, the ends of the organ ride up onto the ridge and are everted. In other words, each end of the organ is turned outward along the circumferential edge of the end so that when the two ends are brought together, the intimae of the organ within the ends are brought into contact with one another.

The thickness of the stent is dependent upon the material used in forming the stent, and is selected to provide the body with sufficient rigidity to support the walls of the organ during suturing, and to separate the opposing walls of the organ from one another to prevent the organ from being sutured closed. The body must be rigid enough to support the walls of the organ, while at the same time being elastic enough to permit penetration by a suture.

The body of the stent is preferably formed of a proteinate including at least two components. One of the components is a protein such as albumin, and the other is a saccharide such as fructose or glucose. The protein is used in the composition because it adds softness and elasticity to the body, and is easily metabolized. The saccharide is more rigid and brittle than the protein, but dissolves or is absorbed more quickly in vivo than the protein.

Preferably, an anticoagulant is also included in the composition of the body. For example, anticoagulants such as Heparin or Coumadin®, both of which are commercially available products, may be used. By including an anticoagulant in the body, the risk of embolic phenomena is reduced.

The composition of the body is selected to provide support to the walls of the organ for the necessary period of time during and subsequent to suturing. However, by controlling the relative amounts of protein and saccharide in the composition, it is possible to provide a construction which dissolves in a matter of minutes to hours after insertion into the body. Thus, it is possible to design the stent for use in any desired application, and to customize the composition in order to ensure that the stent dissolves once it is no longer necessary.

Although the stent is illustrated as being formed of a solid circumferential wall of material, it is also possible to form the body of a circumferential wall having a plurality of radially extending openings communicating between the inner and outer surfaces of the body. The resulting construction presents a lattice or mesh-like wall having an increased surface area which expedites dissolution of the stent once it is inserted into the organ.

Figure 3:
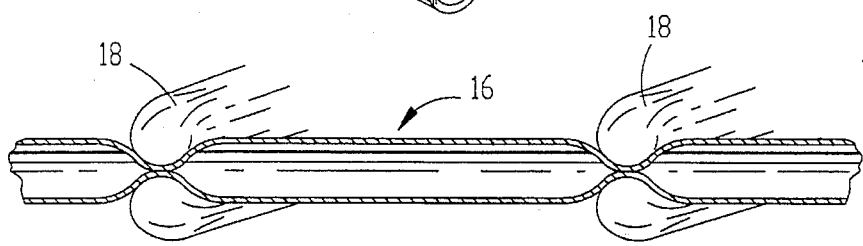
FIG. 3 is a side elevational view of a tubular organ prior to the removal of a damaged section of the organ.
Figure 4:
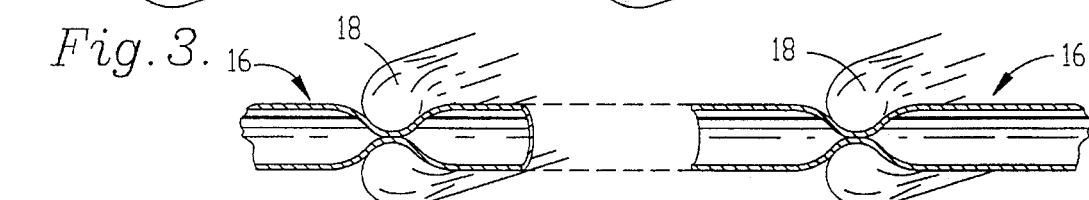
FIG. 4 is a side elevational view of the organ, illustrating removal of the damaged section.

Turning to FIG. 3, a tubular organ 16 such as a blood vessel is illustrated prior to the removal of a damaged section of the vessel. In order to remove the damaged section, the vessel is clamped in a conventional fashion by dog clamps 18 or the like on either side of the damaged section. Thereafter, as shown in FIG. 4, the damaged section is removed.

Figure 5:
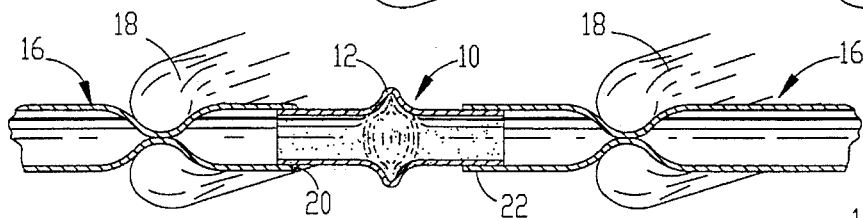
FIG. 5 is a side elevational view of the organ, illustrating an initial step of the anastomotic procedure employing the stent of the preferred embodiment.
Figure 6:
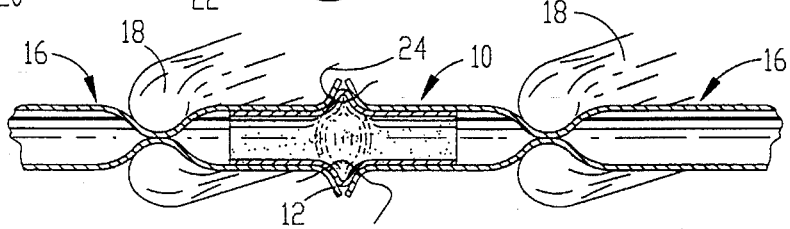
FIG. 6 is a side elevational view of the organ, illustrating an initial suturing step of the anastomotic procedure.
Figure 7:
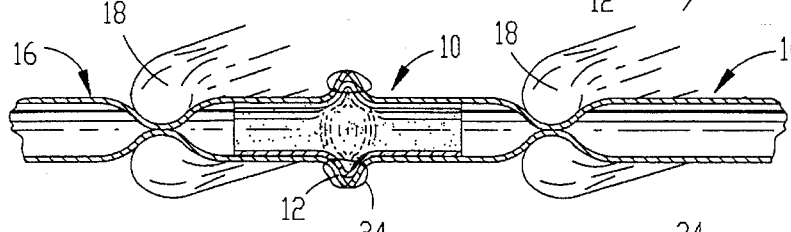
FIG. 7 is a side elevational view of the organ, illustrating a subsequent suturing step.

In order to join the ends 20, 22 of the vessel together, a stent constructed in accordance with the preferred embodiment is inserted into the ends of the vessel, as shown in FIG. 5. The ends of the vessel are pulled completely onto the stent so that they are each everted and lay on the ridge of the stent in contact with one another. As shown in FIG. 6, once the ends of the vessel are brought together on the stent, an initial number of sutures 24 are passed through the vessel 16 and the ridge 12 of the stent in order to tie the ends of the vessel together.

By suturing the vessel at a few equally spaced locations around the circumference thereof, it is possible to then remove the clamps 18 prior to completing the suturing step. Thus, the vessel need only be clamped for a minimal period of time, and the stent substantially seals the vessel against leakage as the suturing operation is continued upon removal of the clamps. An important result of this feature of the invention is that it minimizes the amount of time the vessel is clamped, and allows free blood flow through the site during a substantial portion of the suturing operation.

Figure 8:
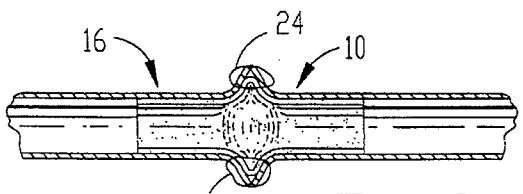
FIG. 8 is a side elevational view of the organ, illustrating the organ upon completion of the procedure.

As shown in FIG. 8, once the clamps are removed from the vessel, suturing of the vessel may continue until the ends of the vessel are securely joined together. Thereafter, as the stent begins to dissolve within the vessel, the circumferential edges presented by the ends of the vessel move back toward their natural, non-everted position. During this movement, the sutures pull the ends of the vessel toward one another so that the intima of each end is continuously held against the intima of the other end, and cellular development at the intersection of these intimae is facilitated. As a result, healing is promoted.

Figure 9:
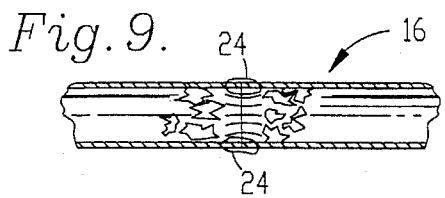
FIG. 9 is a side elevational view of the organ, illustrating the organ as the stent dissolves.

The vessel is illustrated in FIG. 9 subsequent to the anastomotic procedure, wherein the stent is undergoing dissolution. The components used in the stent are thereafter metabolized or otherwise passed through the system.

Although the present invention has been described with reference to the preferred embodiment illustrated in the attached drawing figures, it is noted that substitutions may be made and equivalents employed herein without departing from the scope of the invention as recited in the claims.

What is claimed is:

1. A surgical stent for use in supporting the walls of a tubular organ during anastomosis, wherein the organ is of a predetermined diameter and presents a pair of opposed ends along which the organ is to be joined, the opposed ends each presenting an intima, the stent comprising:

a tubular body having an outer surface, and including opposed axial ends each presenting a cylindrical outer surface section defining a diameter about equal to the diameter of the organ, the body including a means for everting the ends of the organ when the ends are positioned on the stent, placing the intimae of the ends of the organ against one another to facilitate suturing, the means for everting the ends of the organ including a single circumferential ridge intermediate the ends of the body, the outer surface of the body being obliquely inclined away from the ridge, the body being formed of a composition including a protein and a saccharide so that the stent dissolves after insertion into the body.

2. A surgical stent as recited in claim 1, wherein the saccharide is absorbed at a quicker rate in vivo than the protein.

3. A surgical stent as recited in claim 1, wherein the composition includes an anticoagulant.

4. A surgical stent as recited in claim 1, wherein the saccharide is fructose.

5. A surgical stent as recited in claim 1, wherein the saccharide is glucose.

6. A method of joining two ends of a tubular organ together comprising the steps of:

clamping the tubular organ adjacent each end and then placing the ends of the organ over the opposed ends of a tubular body, the tubular body having a diameter about equal to the diameter of the organ and including a circumferential ridge intermediate the ends;

pushing the ends of the organ into contact with one another atop the ridge of the tubular body so that the ends of the organ are everted;

suturing the ends of the organ together through the ridge of the tubular body, wherein the tubular body supports the organ during suturing; and unclamping the tubular organ during the suturing step.

* * * * *